(12) United States Patent
Nielsen et al.

(10) Patent No.: US 7,349,618 B2
(45) Date of Patent: Mar. 25, 2008

(54) OPTICAL FEEDTHROUGH ASSEMBLY FOR USE IN IMPLANTABLE MEDICAL DEVICE

(75) Inventors: Christian S. Nielsen, River Falls, WI (US); Timothy T. Bomstad, Inver Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/380,248

(22) Filed: Apr. 26, 2006

(65) Prior Publication Data

US 2007/0253673 A1  Nov. 1, 2007

(51) Int. Cl.
G02B 6/00 (2006.01)
G02B 6/26 (2006.01)
G02B 6/42 (2006.01)

(52) U.S. Cl. .................................. 385/138; 385/25
(58) Field of Classification Search ................ 385/138, 385/25
See application file for complete search history.

(56) References Cited

U.S. PATENT DOCUMENTS

| | | | |
|---|---|---|---|
| 4,421,382 A * | 12/1983 | Doi et al. | 385/137 |
| 4,703,757 A | 11/1987 | Cohen | |
| 5,188,632 A * | 2/1993 | Goldenberg | 606/7 |
| 5,454,807 A * | 10/1995 | Lennox et al. | 606/15 |
| 5,833,682 A * | 11/1998 | Amplatz et al. | 606/15 |
| 5,964,751 A * | 10/1999 | Amplatz et al. | 606/15 |
| 6,445,939 B1 * | 9/2002 | Swanson et al. | 600/342 |
| 6,554,794 B1 * | 4/2003 | Mueller et al. | 604/95.04 |
| 6,865,317 B2 * | 3/2005 | Vahala et al. | 385/30 |
| 6,891,996 B2 * | 5/2005 | Sercel et al. | 385/30 |
| 6,959,140 B2 | 10/2005 | Cens et al. | |
| 2004/0052476 A1 * | 3/2004 | Houmault | 385/88 |
| 2004/0197051 A1 * | 10/2004 | Sercel et al. | 385/39 |
| 2005/0206021 A1 * | 9/2005 | Elomaki et al. | 264/1.28 |
| 2005/0232811 A1 * | 10/2005 | Autschbach et al. | 422/44 |

\* cited by examiner

*Primary Examiner*—K. Cyrus Kianni
(74) *Attorney, Agent, or Firm*—Carol F. Barry; Steve Bauer (57) ABSTRACT

An optical feedthrough assembly is provided that is configured to be disposed through the canister of an implantable medical device. The optical feedthrough assembly comprises a ferrule having an aperture therethrough and an inner surface therethrough. An optical fiber passes through the aperture, and a compression seal stack is disposed within the aperture and around the optical fiber. The compression seal stack sealingly engages the optical fiber and the inner surface.

7 Claims, 5 Drawing Sheets

OPTICAL FEEDTHROUGH ASSEMBLY FOR USE IN IMPLANTABLE MEDICAL DEVICE

TECHNICAL FIELD

This invention relates generally to implantable medical devices and, more particularly, to an optical feedthrough assembly for use in an implantable medical device.

BACKGROUND OF THE INVENTION

Implantable medical devices (IMDs) are now being equipped with biosensor systems capable of monitoring optical characteristics (e.g., changes in refractive index or reflectivity) indicative of physiological conditions (e.g., temperature, pressure, blood oxygen content, rate of chemical processing, etc.). An IMD may now be equipped with, for example, a fiber-linked optical interferometric system capable of monitoring hydrostatic pressure at a chosen site within a patient's body; e.g., blood pressure within an artery. In such a system, the proximal end of a flexible, elongated catheter is coupled to an IMD and the distal end of the catheter is positioned adjacent the site to be optically monitored. The catheter carries an optical fiber, which is optically coupled to a transceiver disposed within the IMD's canister. The transceiver directs outgoing light signals into the proximal end of the fiber, which propagate through the optical fiber until they reach the fiber's distal end. The light signals are then modulated by the body fluid (e.g., blood) being monitored and are reflected back into the fiber. The modulated signals propagate through the optical fiber once again and are received by the transceiver at the fiber's proximal end. The transceiver analyzes characteristics (e.g., amplitude in an interferometer) of the returning signals, and control circuitry coupled to the transceiver determines the blood pressure at the distal end of the catheter.

An optical feedthrough is utilized to guide the optical fiber through the canister of the IMD. The feedthrough may comprise a ferrule (e.g., titanium) having an aperture therethrough through which the optical fiber passes. To protect the circuitry of the IMD and to secure the optical fiber within the ferrule, a hermetic seal is formed between an inner surface of the ferrule and an outer surface of the optic fiber. Traditionally, the hermetic seal has typically been formed by way of a co-firing or brazing process. For example, a window-ferrule braze may be formed by threading an annular ceramic or metal (e.g., gold) preform over the window and positioning the preform against an inner shelf provided within the ferrule. If a matched seal is to be formed, the components are chosen to have similar coefficients of thermal expansion, and an inner surface of the ferrule may be metalized prior to insertion of the preform. Next, the feedthrough assembly is heated in a furnace (e.g., to over 700 degrees Celsius for approximately 10-15 minutes) to cause the brazing compound to wet the glass and flow against the ferrule to form a seal. An annealing step is then performed, and the feedthrough assembly is allowed to cool to room temperature.

Glass-to-metal seals are relatively rigid and thus may crack if placed under significant mechanical and thermal stress, which may promote the chemical degradation of the seal. Furthermore, conventional co-firing or brazing processes utilized to produce glass-to-metal and ceramic-to-metal seals subject the optical fiber, or window, to extreme temperatures and thus limit the materials from which the fiber may be made, notably eliminating from consideration plastic optic fibers (POFs) made from flexible and low-cost polymers such as polymethylmethacrylate (PMMA), polystyrene, and polycarbonate. Additionally, co-firing and brazing processes may be relatively complex, costly, and time consuming to perform.

In view of the above, it should be appreciated that it would be desirable to provide an optical feedthrough assembly suitable for use in conjunction with optical fibers comprising a wide range of materials, including POFs. In addition, it would be advantageous if such an optical feedthrough assembly employed a polymeric compression seal that tolerates mechanical stress relatively well and that exhibits a high degree of resistance to chemical degradation. It would be of further benefit if such feedthrough assembly could be manufactured economically and efficiently. Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed descriptions. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
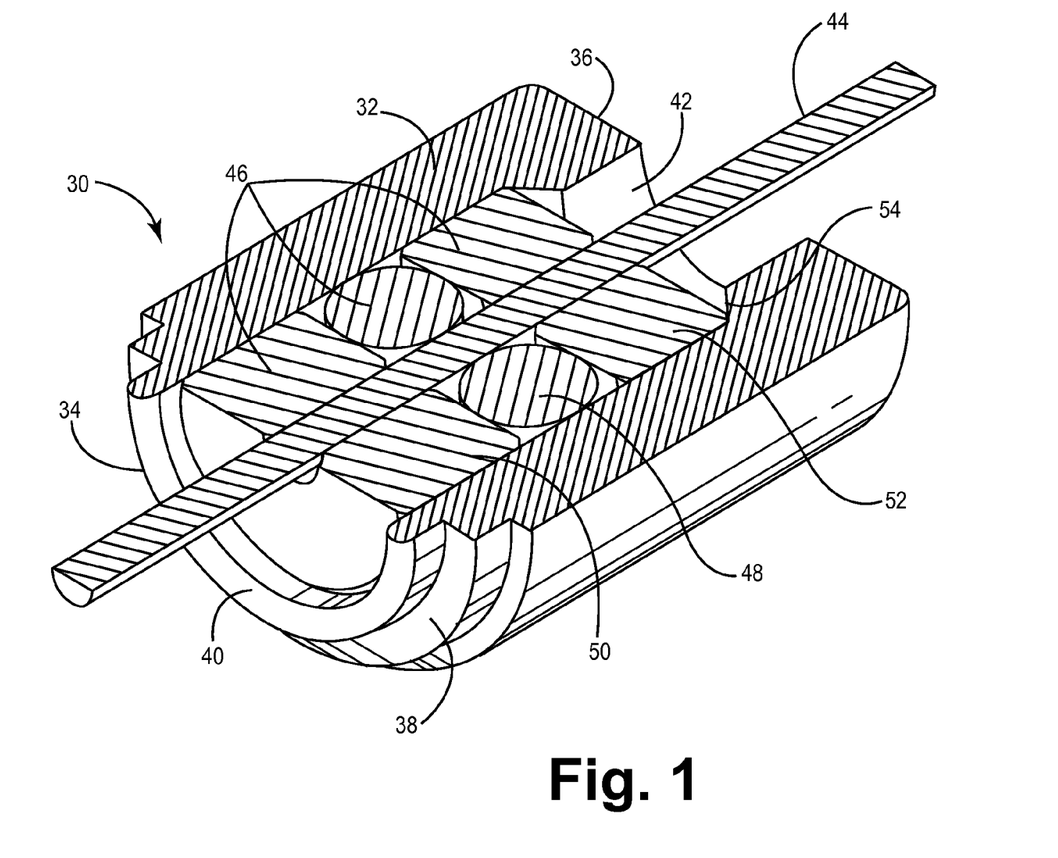
FIGS. 1 and 2 are an isometric cross-sectional and side cross-sectional views, respectively, of an optical feedthrough assembly in accordance with a first embodiment of the present invention.
Figure 2:
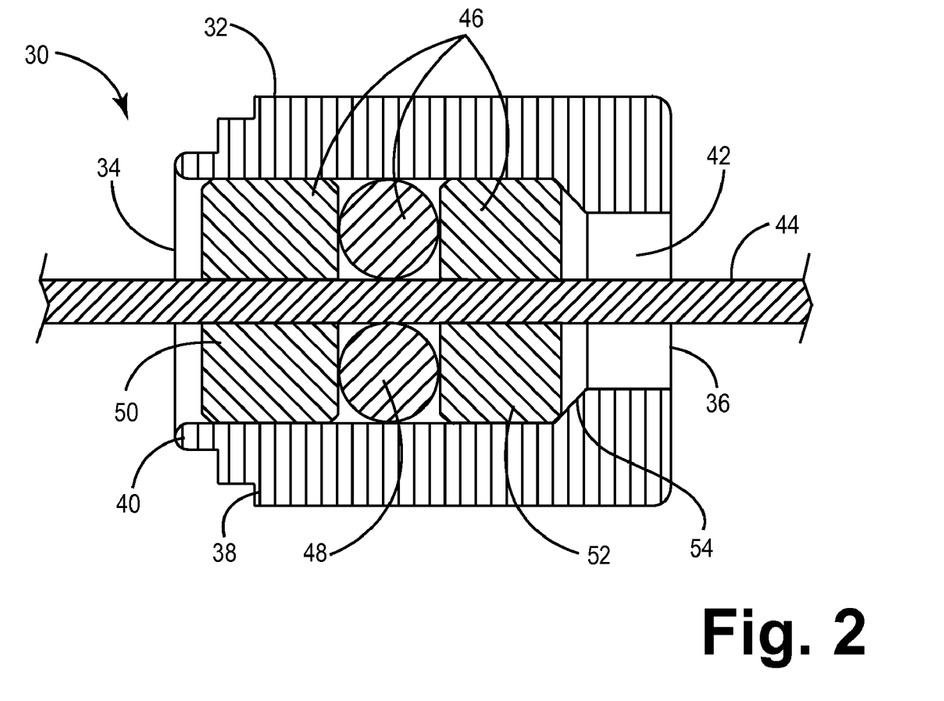

FIGS. 1 and 2 are isometric cross-sectional and side cross-sectional views, respectively, of an optical feedthrough assembly 30 in accordance with a first embodiment of the present invention. Feedthrough assembly 30 comprises a ferrule 32 (e.g., titanium) having a first end region 34 and a second end region 36. End region 34 includes an outer stepped portion 38 that may be fixedly coupled (e.g., welded) to the canister of an implantable medical device as described more fully below in conjunction with FIG. 7. End region 34 also includes a retaining portion 40, which may be, for example, a crimpable collar. A generally cylindrical cavity 42 extends through ferrule 32 from end region 34 to end region 36. An optical fiber 44 passes through cavity 42. Optical fiber 44 may be a multi-mode or single mode fiber. The core of optical fiber 44 comprises an optically transparent material through which light signals may be transmitted. The core of optical fiber 44 may comprise, for example, glass (e.g., silica), quartz, or any one of a variety of polymers, including polymethylmethacrylate (PMMA), polystyrene, and polycarbonate. The core of optical fiber 44 may be sheathed in a cladding (e.g., silica glass) having an index of refraction slightly higher than that of the fiber's core. Light signals introduced into the proximal end of the core of fiber 44 will successively internally reflect off the cladding and thus propagate axially along the fiber's core until they reach the distal end of optical fiber 44. However, it should be appreciated that many optical fibers (e.g., POFs) do not require an outer cladding to achieve total internal reflection, including optical fibers that are of a relatively short length, such as those utilized as optical windows.

A polymeric compression seal stack 46 is disposed within ferrule 32 and guides optical fiber 44 through cavity 42. Compression seal stack 46 may comprise a wide variety of components and configurations; however, in the illustrated embodiment, compression seal stack 37 comprises three components: (1) a compression ring 48, (2) a first compression ring seat 50, and (3) a second compression ring seat 52. Compression ring 48 and ring seats 50 and 52 each have a generally ring-shaped geometry including a central aperture therethrough for receiving fiber 44. Compression seal stack 46 is formed as ring seat 52, compression ring 48, and ring seat 50 are each threaded over fiber or window 44 in succession and inserted into ferrule 32 through end region 34. Compression seal stack 46 is prevented from exiting ferrule 32 through end region 36 by an inner step 54, which abuts ring seat 52 as shown in FIGS. 1 and 2.

Figure 3:
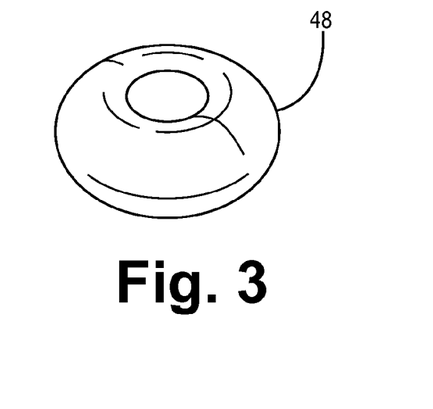
FIG. 3 is an isometric view of the compression ring shown in FIGS. 1 and 2.

Compression ring 48 may assume a variety of forms; for example, as shown in FIG. 3, compression ring 48 may assume a generally torroidal form having a generally circular cross-section. Compression ring 48 is preferably made of a compressible silicon-based material, although other compressible materials may be utilized, including a flouroelastomer co-polymer of vinylidene fluoride and hexaflouropropylene, ethylene propylene diene monomer rubber, polychloroprene, acrylonitrile butadiene co-polymer, and/or polysulphide. As ring 48 may be made of a polymeric material, compression ring 48 may tolerate mechanical stress and resist chemical degradation more effectively than prior art glass- or ceramic-to-metal seals. In contrast to compression ring 48, compression ring seats 50 and 52 comprise a more rigid material. For example, compression rings seats 50 and 52 may be made from hard plastic, glass, porcelain, alumina, or chromium doped alumina. Alternatively, ring seats 50 and 52 may be machined from a metal or alloy. If ring seats 50 and 52 may come into contact with biological fluids, the material chosen for ring seats 50 and 52 should obviously be biocompatible (e.g., a biocompatible metal, such as titanium, stainless steel, cobalt-chromium alloys, or tantalum).

When force is applied to compression ring seat 50 in the direction of compression ring seat 52, compression ring 48 is compressed between seats 50 and 52. This causes compression ring 48 to radially expand and sealing engage an outer diameter of optical fiber 38 and an inner surface of ferrule 32. A hermetic seal is thus formed within ferrule 32. After compression seal stack 46 has been compressed in this manner, collar 40 may be subsequently crimped (i.e., deformed inward) to contact ring seat 50 and thus secure compression seal stack 46 in its compressed state. Compression and crimping of optical feedthrough assembly 30 may be accomplished through the use of a compression and crimping tool, such as that described below in conjunction with FIGS. 5 and 6.

Figure 4:
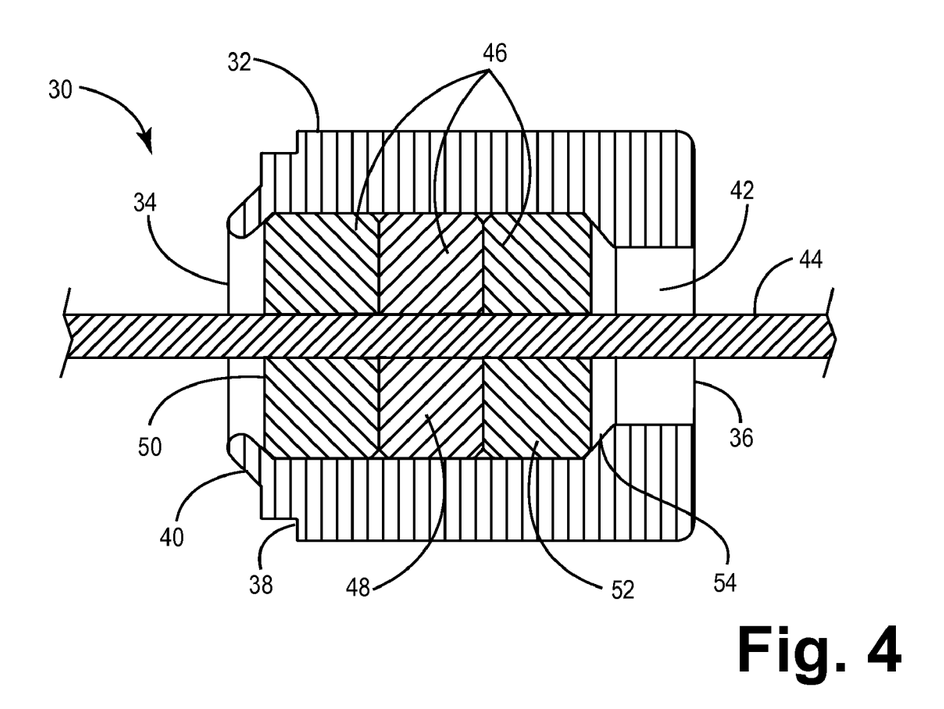
FIG. 4 is a cross-sectional view of the optical feedthrough assembly shown in FIGS. 1 and 2 after compression and crimping.
Figure 5:
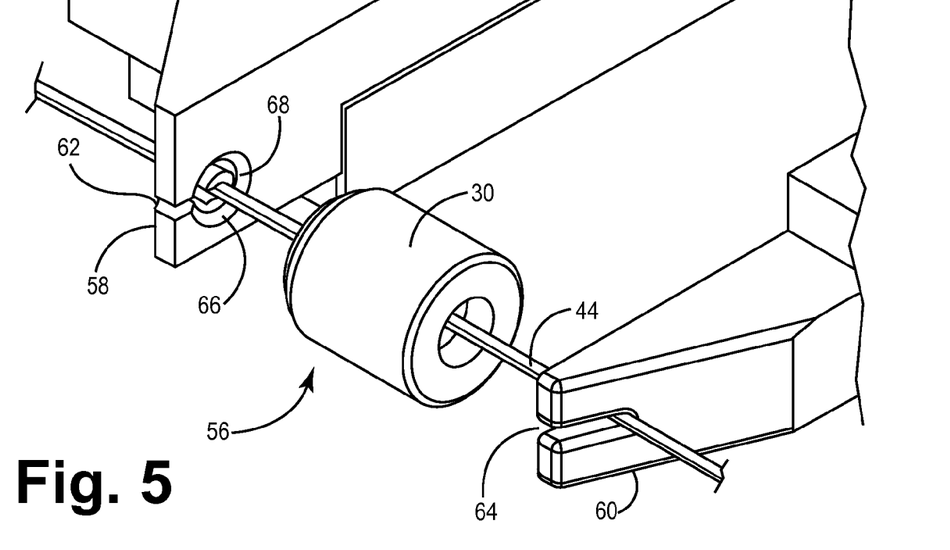
FIG. 5 is an isometric view of an apparatus suitable for compressing and crimping the optical feedthrough assembly show in FIGS. 1, 2, and 4.
Figure 6:
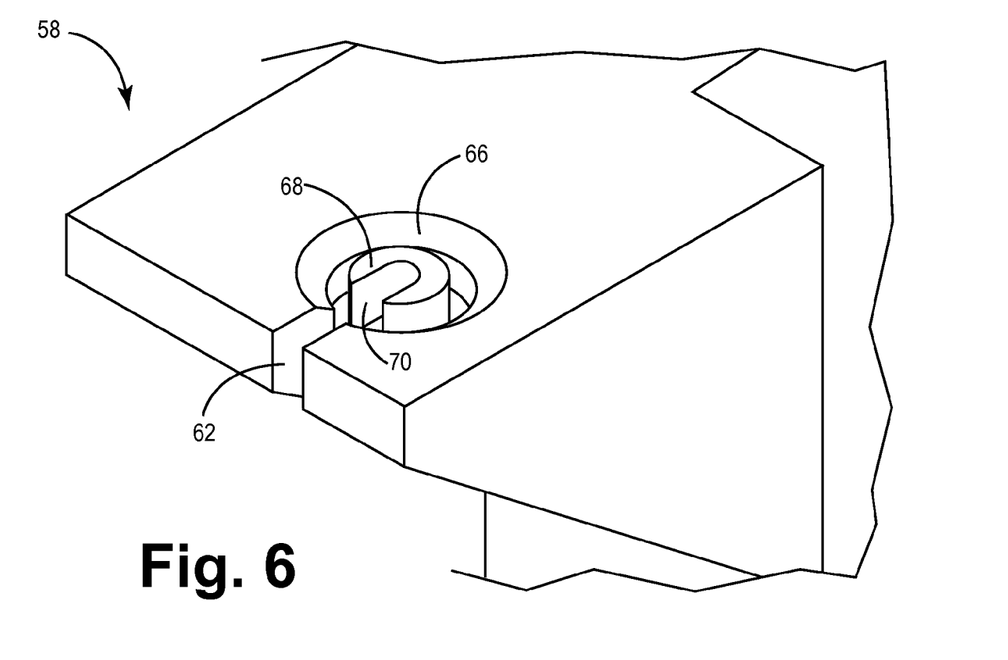
FIG. 6 is a more detailed isometric view of the lower jaw of the apparatus illustrated in FIG. 5.

FIG. 5 illustrates a compression and crimping apparatus 56 suitable compressing seal stack 46 and crimping collar 40 of optical feedthrough assembly 30 (FIGS. 1, 2, and 4). Apparatus 56 comprises a first compression jaw 58 and a second compression jaw 60 (shown in greater detail in FIG. 6). Jaws 58 and 60 are coupled to a track (not shown) and may move relative to one another in a clamp-like fashion. To facilitate production, compression jaws 58 and 60 may be incorporated into an automated system. Typically, the compressing and crimping process is performed after feedthrough assembly 30 is welded to the canister of an implantable medical device; however, feedthrough assembly 30 is shown independently in FIGS. 5 and 6 for clarity.

Compression jaws 58 and 60 include respective openings 62 and 64 (e.g., two slots) for receiving therein upper and lower segments of optical fiber 38. Compression jaw 58 further includes a well portion 66 having a generally inclined surface. An island 68 having an opening 70 therein protrudes upward from a central portion of well 66. The compression and crimping process begins as optical feedthrough assembly 30 is loaded onto apparatus 56 and optical fiber 44 is received in openings 62, 64, and 66 as shown in FIG. 5. Next, jaws 58 and 60 are moved toward one another such that jaw 58 engages ferrule 32 proximate end portion 34 and jaw 60 engages ferrule 32 proximate end portion 36. Island 68 extends into cavity 42 proximate end portion 34 to contact compression ring seat 50. This forces ring seat 50 towards ring seat 52 thus compressing ring 48 between seats 50 and 52. As explained above, this results in the formation of a hermetic seal within ferrule 32. After seal stack 46 (FIGS. 1, 2, and 4) has been compressed in this manner, well 66 engages ferrule 32 and crimps collar 40. That is, the included surface of well 66 bears against collar 40 and causes collar 40 to deform inward over ring seat 50. In this way, collar 40 secures compression seal stack 46 in its compressed state and thus maintains the integrity of the hermetic seal within ferrule 32. Considering the forgoing paragraphs, it should be appreciated that the above-described compression and crimping process may be performed with less cost and more efficiently than conventional co-firing or brazing processes that require the heating and cooling of glass or ceramic preforms.

Figure 7:
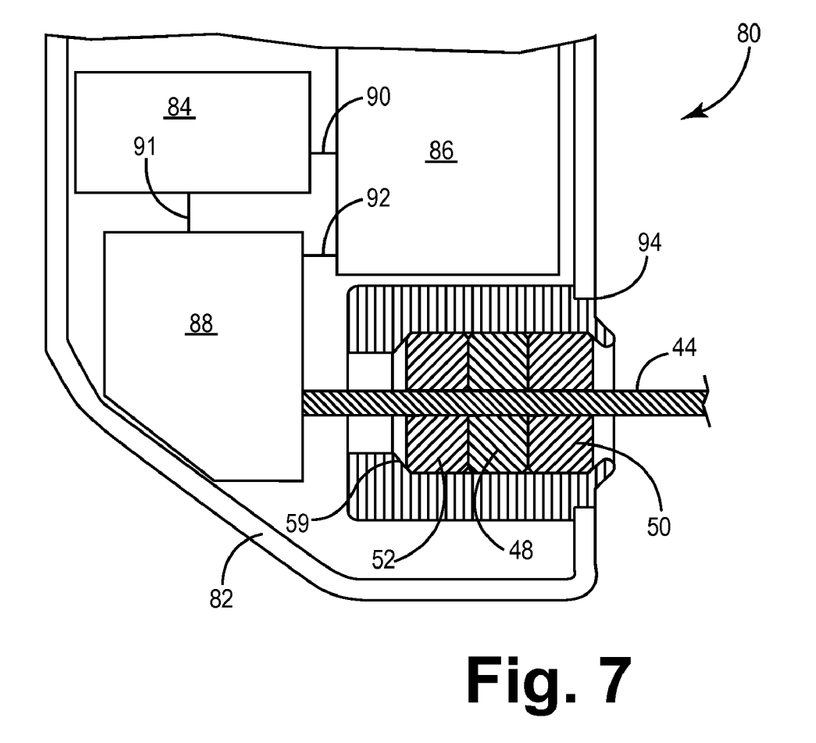
FIG. 7 is a cross-sectional view of an implantable medical device employing the optical feedthrough assembly shown in FIGS. 1, 2, and 4.

FIG. 7 is a functional view of a portion of an implantable medical device (IMD) 80 incorporating optical feedthrough assembly 30 shown in FIGS. 1, 2 and 4. IMD 80 comprises a canister 82 (e.g., titanium, aluminum, stainless steel, etc.) that houses control circuitry 84, a battery 86, and a transceiver 88. Battery 86 is coupled to control circuitry 84 and to transceiver 88 as is shown at 90 and 92, respectively. In addition, control circuitry 84 is electrically coupled to transceiver 88 as is shown at 91. An aperture 94 is provided through canister 82 to accommodate feedthrough assembly 30. Assembly 30 is disposed through aperture 94 and fixedly coupled (e.g., welded) to canister 82 proximate outer stepped portion 38. An elongated, flexible catheter (not shown for clarity) is coupled to canister 82 proximate feedthrough assembly 30 to receive optical fiber 44 from assembly 30. Optical fiber 44 is optically coupled to transceiver 88, and may (or may not) be physically coupled to transceiver 88. Transceiver 88 includes a light source (e.g., a monochromatic light source, such as a light emitting diode or laser) and a light detector. Transceiver 88 directs outgoing light signals into the proximal end of fiber 44 and detects returning, modulated light signals at the proximal end of fiber 44. Transceiver 88 converts the returning light signals into electrical signals and provides them to control circuitry 84. Control circuitry 84 utilizes the electrical signals received from transceiver 88 to determine, for example, the current status of a physiological condition within a patient's body.

Figure 8:
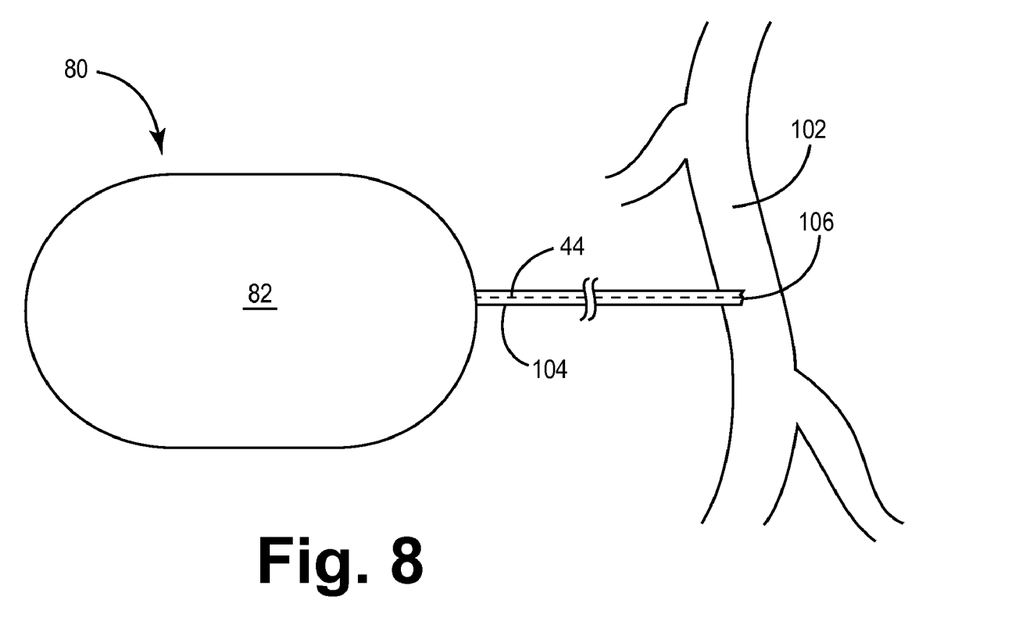
FIG. 8 is an isometric view of the implantable medical device shown in FIG. 7 implanted within a patient's body.

IMD 80 may optically monitor a wide variety of physiological conditions within a patient's body. For example, as shown in FIG. 8, IMD 80 may serve as an optical interferometer capable of monitoring systolic and diastolic pressure within an artery 102 (e.g., the femoral or brachial artery). As can be seen in FIG. 8, optical fiber 44 extends through canister 82 and into an elongated and flexible catheter 104. Optical fiber 44 extends axially through the body of catheter 104; however, the distal tip of fiber 44 terminates a short distance away from the distal end of catheter 104 such that a small gap exists between the distal tip of fiber 44 and the distal end catheter 104. The distal end of catheter 104 is covered by a reflective diaphragm 106 (e.g., a silicon or polymer membrane). Diaphragm 106 may flex at its center and thus move closer to, or further away from, the distal tip of optical fiber 44. When the distal end of catheter 104 is inserted into artery 102 as shown in FIG. 8, diaphragm 106 is placed in fluid contact with blood flowing through artery 102. Consequently, diaphragm 106 will flex (i.e., extend partially into the distal of catheter 104) in relation to the pressure exerted thereon by the blood flowing through artery 102.

As stated above, transceiver 88 emits light signals into the proximal end of fiber 44. The outgoing light signals propagate through fiber 44 to the distal end of catheter 104. When reaching the distal tip of fiber 44, the light signals exit fiber 44 and strike diaphragm 106. The light signals reflect from diaphragm 106, reenter the distal tip of fiber 44, and return to the proximal end of fiber 44 monitored by transceiver 88. It should thus be appreciated that the length of the optical path traveled by the light signals emitted by transceiver 88 corresponds to the position of diaphragm 106 relative to the distal tip of fiber 44. Due to interference between the reflected light signals and emitted outgoing light signals, the resulting amplitude of the sensor portion of the transceiver will vary depending upon optical path length. Transceiver 88 measures the amplitude of the returning light signals and converts this measurement into electrical signals that control circuitry 84 may utilize to determine the pressure exerted on diaphragm 106 and, therefore, the systolic or diastolic pressure within artery 102.

Figure 9:
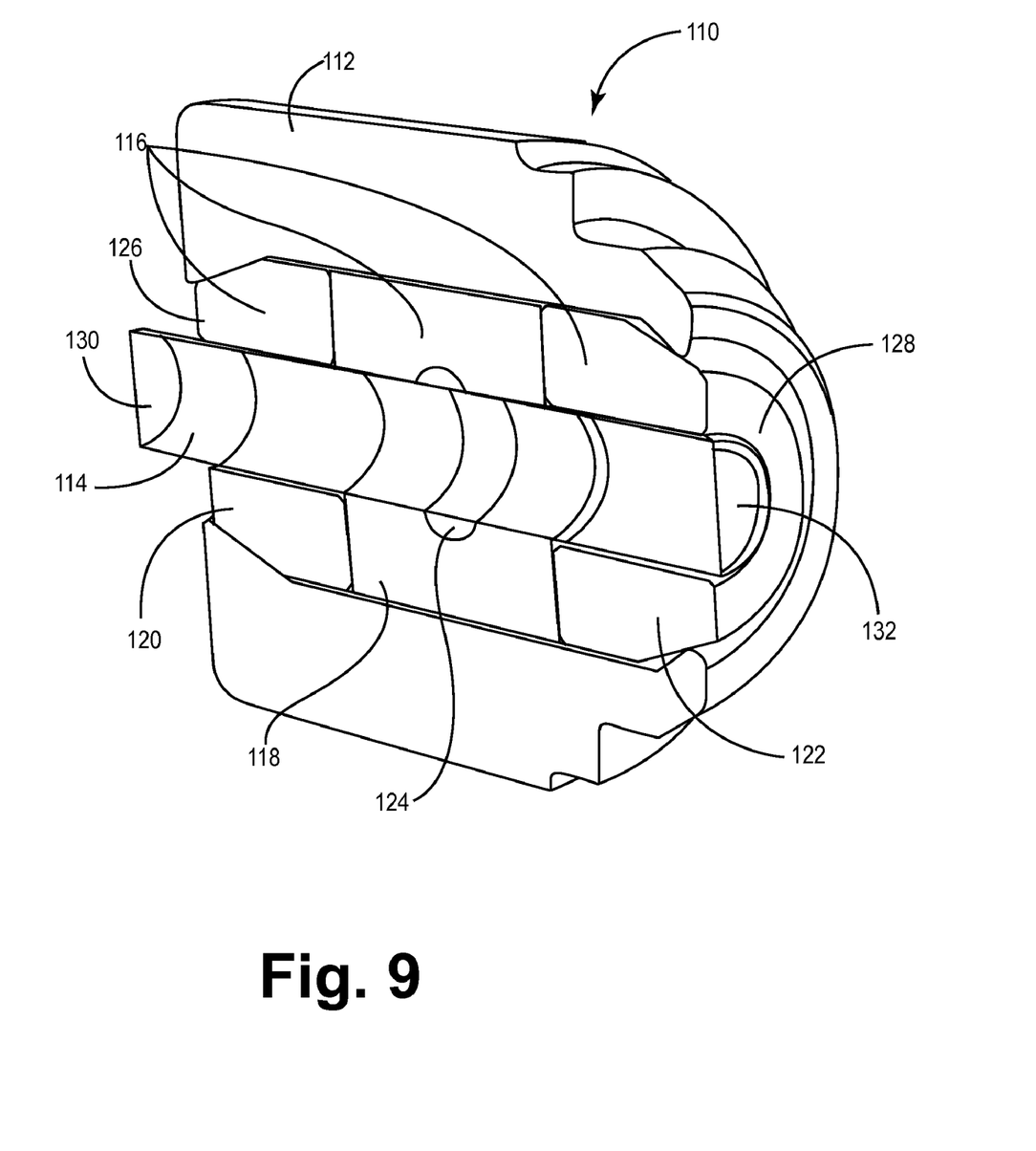
FIG. 9 is an isometric cross-sectional view of an optical feedthrough assembly employing a truncated fiber or window in accordance with a second embodiment of the present invention.

FIG. 9 is an isometric cross-sectional view of an optical feedthrough assembly 110 in accordance with a second embodiment of the present invention. Feedthrough assembly 110 is similar in many respects to assembly 30 described above in conjunction with FIGS. 1, 2, and 4; i.e., assembly 110 comprises a ferrule 112, an optical fiber 114 passing through ferrule 112, and a compression seal stack 116 disposed within ferrule 112 and around fiber 114. Compression seal stack 116 comprises a compression ring 118 and two compression ring seats 120 and 122. Unlike assembly 30, however, compression ring 118 has a generally tubular shape and includes an annular depression 124 in a medial portion thereof to facilitate compression of ring 118. Also unlike assembly 30, compression ring seats 120 and 122 include tapered ends 126 and 128, respectively. Lastly, fiber 114 comprises a relatively short segment having a first end 130 that terminates proximate compression ring seat 126 and a second end 132 that terminates proximate compression ring seat 128. As will be appreciated by one skilled in the art, this type of window configuration may be useful if feedthrough assembly 110 is employed in conjunction with, for example, a blood oxygen monitoring system.

Although certain embodiments of the present invention were described above as utilizing a window-type fiber (e.g., assembly 110 shown in FIG. 9) while others were described as employing an optical fiber extending substantially beyond the ends of the ferrule (e.g., assembly 30 shown in FIGS. 1, 2, 4, and 7), it should be understood that the invention is not limited to these embodiments and may incorporate optical fibers of a wide variety of lengths and types. Furthermore, the term "optical fiber" appearing herein is used in its broadest sense and includes relatively short fibers utilized to form optical windows.

In view of the above, it should be appreciated that an optical feedthrough assembly has been provided that is suitable for use in conjunction with optical fibers comprising a wide range of materials, including various polymers. It should further be appreciated that the inventive optical feedthrough incorporates a polymeric compression that may be manufactured economically and efficiently. Although the invention has been described with reference to a specific embodiment in the foregoing specification, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

What is claimed is:

1. An implantable medical device (IMD) comprising:
   an optical feedthrough assembly configured to be disposed through a canister of the IMD, the optical feedthrough assembly includes:
      a ferrule having an aperture therethrough and an inner surface therethrough;
      an optical fiber passing through the aperture; and
      a compression seal stack disposed within the aperture and around said optical fiber, said compression seal stack sealingly engaging said optical fiber and said inner surface.

2. An optical feedthrough assembly according to claim 1 wherein said compression stack comprises:
   a compression ring disposed within the aperture and around said optical fiber, said compression ring sealingly engaging said optical fiber and said inner surface; and
   at least one ring seat disposed within the aperture adjacent said compression ring.

3. An optical feedthrough assembly according to claim 2 wherein said at least one ring seat comprises a first ring seat and a second ring seat, said compression ring disposed intermediate said first ring seat and said second ring seat.

4. An optical feedthrough assembly according to claim 3 wherein said ferrule includes an inner stepped portion abutting said first ring seat.

5. An optical feedthrough assembly according to claim 3 wherein said ferrule includes a crimpable portion to contact said second ring seat to maintain said compression seal stack in a compressed state.

6. An optical feedthrough assembly according to claim 1 wherein said at least one ring seat includes a tapered portion substantially opposite said compression ring.

7. An optical feedthrough assembly according to claim 1 wherein said optical fiber has a first end disposed proximate said ferrule.

* * * * *

UNITED STATES PATENT AND TRADEMARK OFFICE
CERTIFICATE OF CORRECTION

| | | |
|---|---|---|
| PATENT NO. | : 7,349,618 B2 | Page 1 of 1 |
| APPLICATION NO. | : 11/380248 | |
| DATED | : March 25, 2008 | |
| INVENTOR(S) | : Christian Nielsen et al. | |

It is certified that error appears in the above-identified patent and that said Letters Patent is hereby corrected as shown below:

Col. 6, lines 46 - 49, delete "An implantable medical device (IMD) comprising: an optical feedthrough assembly configured to be disposed through a canister of the IMD, the optical feedthrough assembly includes:" and insert in place there of --An optical feedthrough assembly configured to be disposed through the canister of an implantable medical device, comprising:--

Signed and Sealed this

Twenty-seventh Day of January, 2009

JOHN DOLL
*Acting Director of the United States Patent and Trademark Office*